(12) United States Patent
Hathaway

(10) Patent No.: US 6,952,257 B2
(45) Date of Patent: Oct. 4, 2005

(54) INSPECTION STATION

(75) Inventor: Darek Brady Hathaway, Chester, VA (US)

(73) Assignee: Philip Morris USA Inc., New York, NY (US)

( * ) Notice: Subject to any disclaimer, the term of this patent is extended or adjusted under 35 U.S.C. 154(b) by 177 days.

(21) Appl. No.: 10/461,300

(22) Filed: Jun. 13, 2003

(65) Prior Publication Data
US 2004/0252294 A1 Dec. 16, 2004

(51) Int. Cl.[7] .............................................. G01N 21/00
(52) U.S. Cl. .................................................. 356/237.2
(58) Field of Search ........................ 356/237.1–237.6, 356/239.1–239.8; 209/535, 536, 588; 131/905–908

(56) References Cited

U.S. PATENT DOCUMENTS

| 3,980,567 | A | | 9/1976 | Benini |
| 4,090,794 | A | | 5/1978 | Benini |
| 4,307,963 | A | | 12/1981 | Bolt |
| 4,486,098 | A | | 12/1984 | Buchegger et al. |
| 4,644,176 | A | * | 2/1987 | Heitmann et al. ..... 250/559.46 |
| 6,384,359 | B1 | | 5/2002 | Belcastro et al. |

* cited by examiner

Primary Examiner—Tu T. Nguyen
(74) Attorney, Agent, or Firm—Connolly Bove Lodge & Hutz LLP

(57) ABSTRACT

An inspection system detects the presence or absence of desired components of multiple component, longitudinally oriented cigarette filter assembly having at least opposite end components and a central component. A transport moves the filter assemblies along a high speed path of travel. At a first inspection station a transverse detection beam is directed toward each filter assembly in the area of the central component, and a receiver detects the reflection of that beam if the central component is present. A second inspection station directs a longitudinal detection beam toward an end filter component along a path substantially parallel to the longitudinal axis of the filter assembly, and a transverse receiver inwardly of the outer end of the filter assembly detects the presence of the longitudinal beam if that end filter component is missing.

8 Claims, 2 Drawing Sheets

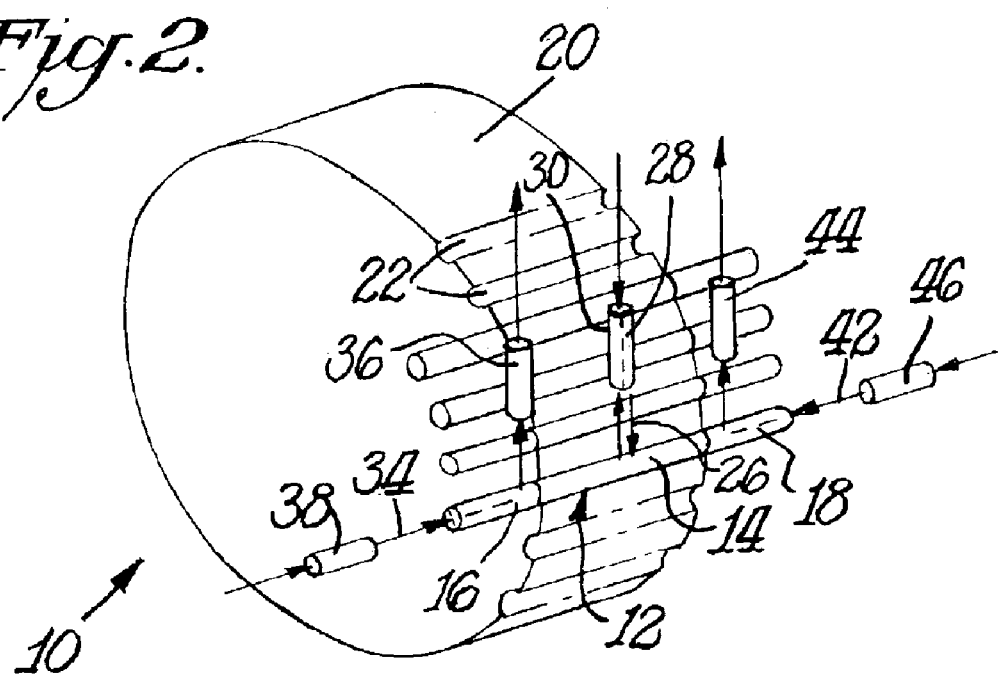

INSPECTION STATION

BACKGROUND OF THE INVENTION

The present invention relates to an inspection system, and more particularly to a filter inspection system for primarily detecting the presence or absence of internal and end filter components of a multiple component filter assembly.

In today's cigarette manufacturing machinery, inspection devices have been proposed that inspect for missing cigarette filters and missing filter segments on cigarettes that require "combined" or multiple component filters. For the most part these inspection systems either inspect for the filter segment prior to the final assembly of the cigarette components, i.e., application of the tipping paper, or inspect only the exposed visible filter end of a completely assembled cigarette. Multiple component filters present a challenge because internal filter components are not visible.

SUMMARY OF THE INVENTION

Accordingly, one of the objects of the present invention is an inspection system that inspects for the presence or absence of internal filter components of a multiple component cigarette filter assembly.

Another object of the present invention is an inspection system which is simple in operation but highly effective and reliable in removing defective filter assemblies from a very high speed stream of filters prior to assembly into cigarettes.

Another object of the present invention is an inspection system that uses fiber optics to inspect for the presence or absence of internal and end filter components.

Still another object of the present invention is an inspection system that inspects for the presence or absence of visible end filter components as well as an internal filter component.

In accordance with the present invention, an inspection system detects the presence or absence of individual components of a multiple component longitudinally oriented cigarette filter assembly having opposite ends. Fundamentally, the inspection system comprises a transport for moving filter assemblies along a path of travel. A first inspection station is constructed and arranged to direct a transverse detection beam is toward each filter assembly in the area of an internal filter component, and to detect the reflection of that beam if the internal component is present. Additionally, at least one second inspection station is constructed and arranged to direct a longitudinal beam toward an end filter component along a path substantially parallel to the longitudinal axis of the filter assembly. A transverse receiver inwardly of the outer end of the filter assembly detects the presence of the longitudinal beam if that end filter component is missing.

A control is constructed and arranged to allow a cigarette filter assembly to continue along a path of travel when the second inspection station determines the presence of an end filter component unless beforehand the first inspection station fails to detect the presence of an internal filter component in which case the second inspection is withheld and the filter assembly is removed from the path of travel.

Preferably the first inspection station includes a fiber optic light emitter and a fiber optic light receiver. Both the emitter and the receiver are positioned on the same side of the filter assembly. The first inspection station detects the presence of an internal filter component when light from the emitter is reflected from that filter component to the receiver.

Preferably the second inspection station also includes a fiber optic light emitter and a fiber optic light receiver. The second inspection station detects the presence of an end filter component when no light is detected by the inwardly spaced receiver. With an end filter present, light from the emitter is effectively blocked and therefore not detected by the receiver.

In a preferred embodiment of the present invention, the transport includes a rotating drum with longitudinal grooves on the exterior surface thereof for receiving the filter assemblies, one in each groove. The inspection stations are appropriately positioned relative to the transport drum for detecting the presence or absence of individual components of each filter assembly.

Preferably a third inspection station is constructed and arranged to detect another longitudinal beam toward the opposite end of the filter assembly along a path substantially parallel to the longitudinal axis of the filter assembly. Another transverse receiver inwardly of the opposite outer end of the filter assembly detects the presence of the other longitudinal beam if the other end filter component is missing. Here again, with an end filter in place, light from the emitter is effectively blocked and therefore not detected by the downstream receiver.

The present invention also includes a method for detecting the present or absence of individual components of a multiple component longitudinally cigarette filter assembly. The method includes the step of moving the filter assembly along a path of travel while conducting first and second inspections to determine the presence or absence of internal and end filter components of the multiple component filter assembly. Fiber optic transmitters and receivers are utilized in conducting the individual inspections.

BRIEF DESCRIPTION OF THE DRAWINGS

Novel features and advantages of the present invention in addition to those mentioned above will be readily apparent to persons of ordinary skill in the art from a reading of the following detailed description in conjunction with the accompanying drawings wherein similar reference characters refer to similar parts and in which:

FIG. 2 is a perspective view showing the transport for the filter assembles and the various components of the inspection system.

DETAILED DESCRIPTION OF THE INVENTION

Figure 1:
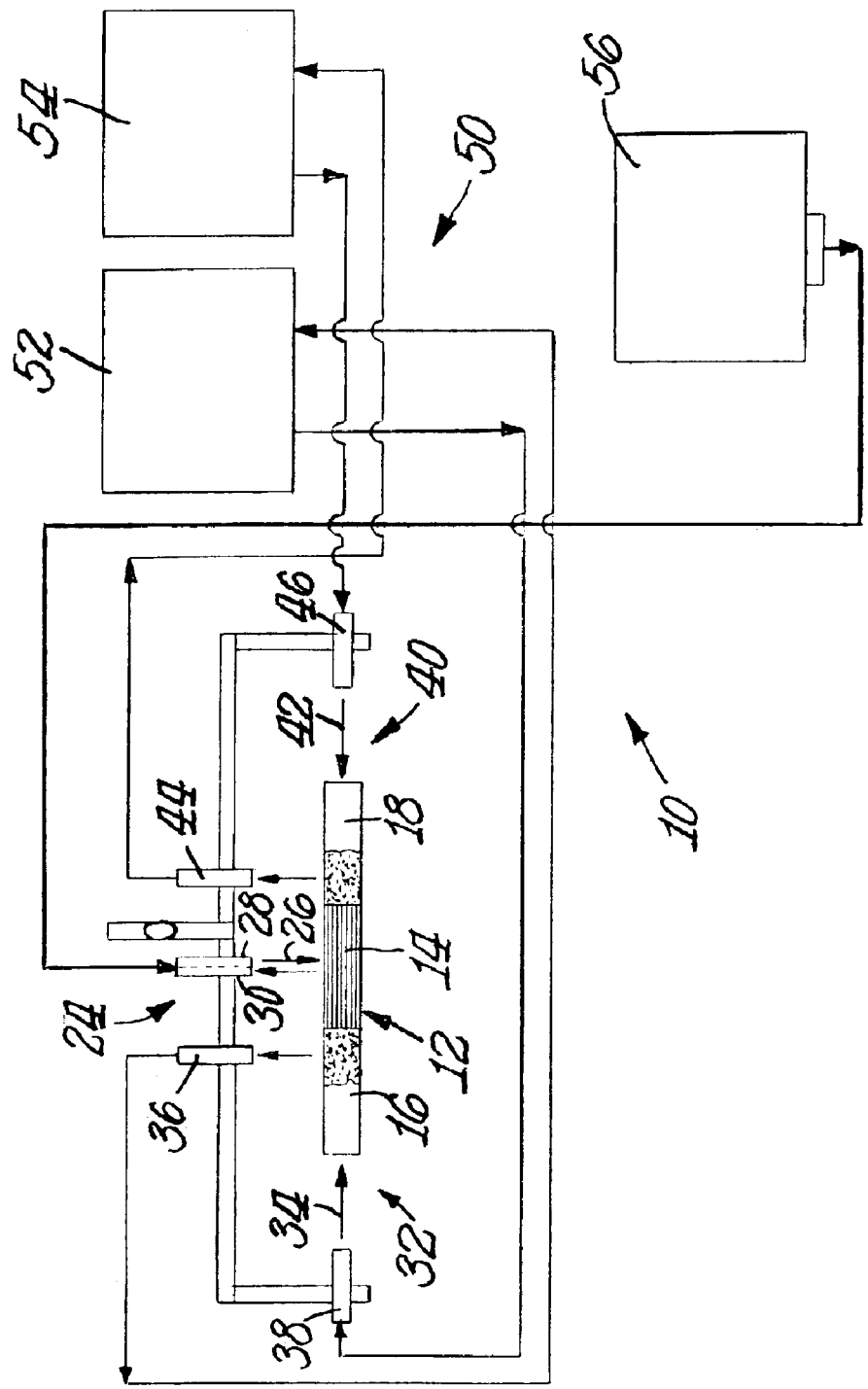
FIG. 1 is a diagrammatic layout illustrating the filter inspection system of the present invention.

Referring in more particularity to the drawing, FIG. 1 basically illustrates a diagrammatic layout of a filter inspection system 10 for detecting the presence or absence of desired components of a multiple component longitudinally oriented cigarette filter assembly 12. In the embodiment illustrated in FIG. 1, filter assembly 12 includes a central cellulose acetate component 14 and opposite end components 16, 18 which may comprise carbon granules, fibers or the like. In actual use, the filter assembly 12 is cut in half mid way between the central component 14 to thereby provide two cigarette filters each having a cellulose acetate component and a carbon component. Tipping paper is used to join each filter to a tobacco rod in the manufacture of cigarettes in a manner well know in the art.

The inspection system 10 includes a transport 20 in the form of a drum, as shown best in FIG. 2. The transport functions to move filter assemblies 12 along a path of travel. Preferably the transport drum includes longitudinal grooves 22 on the exterior surface thereof for receiving the filter assemblies 12, one in each groove.

Filter inspection system 10 includes a first inspection station 24 constructed and arranged to direct a transverse beam 26 toward each filter assembly 12 in the area of the internal filter component 14, and to detect the reflection of the transverse beam 26 if the internal filter component 14 is present. In the preferred embodiment of the invention, the first inspection station includes a fiber optic light emitter 28 and fiber optic light receiver 30. Both the emitter and the receiver are positioned on the same side of the filter assembly 12 as diagrammatically shown in FIG. 1. The first inspection station 24 detects the presence of internal filter component 14 when the light beam 26 from emitter 28 is reflected from the filter component 14 to the receiver 30. If no filter component 14 is present the light beam 26 simply passes through the filter assembly and is not reflected back to the emitter thereby singling that the central component 14 is missing.

Filter inspection system 10 further includes a second inspection station 32 constructed and arranged to direct a longitudinal beam 34 toward end filter component 16 along a path substantially parallel to the longitudinal axis of the filter assembly 12. A transverse receiver 36 spaced inwardly of the outer end of filter assembly 12 detects the presence of longitudinal beam 34 if end filter 16 is missing. When the end filter component is missing the longitudinal beam 34 passes into the space normally occupied by end filter 16, and the beam is readily detected by the transverse receiver 36 thereby indicating the absence of end filter component 16.

The longitudinal beam 34 may be generated by a fiber optic light emitter 38 and the transverse receiver 36 may also be a fiber optic light receiver. Here again the second inspection station 32 detects the presence of end filter component 16 when no light is detected by receiver 36. Under these circumstances the end component 16 blocks the light from entering into the filter assembly in which case no light is detected by the receiver 36.

The filter inspection system of the present invention also includes a third inspection station 40 constructed and arranged to direct another longitudinal beam 42 toward the other end filter component 18 along a path substantially particular to the longitudinal axis of cigarette filter assembly 12. A transverse receiver 44 inwardly of end filter component 18 detects the presence of the longitudinal beam 42 if the end filter component 18 is missing. A fiber optic light emitter 46 may be used to generate the longitudinal beam 42 and receiver 44 may be a filter optic light receiver. Basically the third inspection station 40 functions in the same manner as the second inspection station 32 to detect the presence or absence of end filter component 18.

A control 50 is constructed and arranged to allow a cigarette filter assembly 12 to continue along the path of travel when the second inspection station 32 determines the presence of end filter component 14 unless beforehand the first inspections station 24 fails to detect the presence of internal filter component 14 in which case the second inspection is withheld and the filter assembly 12 is ultimately removed from the path of travel. The same control applies to the third inspection station 40, and overall the control operates to remove a cigarette filter assembly when any one of the three components thereof is missing. An amplifier 52 may be connected to transmit and receive light beams 34 at the second inspection station 32 and a similar amplifier 54 is connected to transmit and receive light beams 42 at the third inspection station 40. Still another amplifier 56 is associated with the first inspection station 24 to transmit and receive light beams 26 associated with the first inspection station.

The present invention also includes a method for detecting the presence or absence of filter components 14, 16, 18 of multiple component cigarette filter assembly 12. The method includes the steps of moving the filter assemblies 12 along a path of travel while conducting first and second inspections of the filter assembly. The first inspection is conducted by directing the transverse detection beam 26 toward each filter assembly 12 in the area of the internal component 14, and detecting the reflection of that beam if the internal filter component is present, in the manner described above. The second inspection is conducted by directing the longitudinal detection beam 34 toward end filter component 16 along a path substantially parallel to the longitudinal axis is the filter assembly 12 and detecting the presence of the longitudinal beam 34 if end filter component 16 is missing. When any of the filter components 14, 16,18 is missing from the filter assembly 12 that particular assembly is removed from the path of travel.

What is claimed is:

1. An inspection system for detecting the presence or absence of desired components of a multiple component longitudinally oriented cigarette filter assembly having opposite ends, the inspection system comprising:

(a) a transport for moving filter assemblies along a path of travel;

(b) a first inspection station constructed and arranged to direct a transverse beam toward each filter assembly in the area of an internal filter component and to detect the reflection of that beam if the internal filter component is present;

(c) a second inspection station constructed and arranged to direct a longitudinal beam toward an end filter component along a path substantially parallel to a longitudinal axis of the filter assembly, and a transverse receiver inwardly of the outer end of filter assembly for detecting the presence of the longitudinal beam if the end filter component is missing;

(d) a third inspection station constructed and arranged to direct another longitudinal beam toward the opposite end of the filter assembly along a path substantially parallel to the longitudinal axis of the filter assembly, and another transverse receiver inwardly of the opposite outer end of the filter assembly for detecting the presence of the other longitudinal beam if the other end filter component is missing; and (e) a control constructed and arranged to allow a cigarette filter assembly to continue along the path of travel when the second and third inspection stations determine the presence of end filter components unless beforehand the first inspection station fails to detect the presence of an internal filter component in which case the second and third inspections are withheld and the filter assembly is removed from the path of travel.

2. An inspection system as in claim 1 wherein the first inspection station includes a fiber optic light emitter and a fiber optic light receiver, both the emitter and receiver positioned on the same side of the filter assembly, and wherein the first inspection station detects the presence of an internal filter component when light from the emitter is reflected from that filter component to the receiver.

3. An inspection system as in claim 1 wherein the second and third inspection stations each include a fiber optic light emitter and a fiber optic light receiver, and wherein the second and third inspection stations detect the presence of end filter components when no light is detected by the receivers.

4. An inspection system as in claim 1 wherein the transport includes a rotating drum with longitudinal grooves on the exterior surface thereof receiving the filter assemblies, one in each groove.

5. A method for detecting the presence or absence of desired components of a multiple component longitudinally oriented cigarette filter assembly having opposite ends, the method comprising the steps of:

(a) moving filter assemblies along a path of travel;

(b) conducting a first inspection by directing a transverse detection beam toward each filter assembly in the area of an internal filter component and detecting the reflection of that beam if the internal filter component is present;

(c) conducting a second inspection by directing a longitudinal detection beam toward an end filter component along a path substantial parallel to a longitudinal axis of the filter assembly, and detecting the presence of the longitudinal beam if the end filter component is missing;

conducting a third inspection by directing a longitudinal detection beam toward the opposite end filter component along a path substantially parallel to the longitudinal axis of the filter assembly, and detecting the presence of that longitudinal beam if the outer end filter component is missing; and (e) allowing a filter assembly to continue along the path of travel when the second and third inspections detect the presence of end filter components unless beforehand the first inspection fails to detect the presence of an internal filter component in which case operation of the second and third inspections is withheld and the filter assembly is removed from the path of travel.

6. A method as in claim 5 wherein the first inspection is a fiber optic light emitter and a fiber optic light receiver, positioning both the emitter and receiver on the same side of the filter assembly.

7. A method as in claim 5 wherein the longitudinal detection beam of each of the second and third inspections is an optical beam.

8. A method as in claim 5 wherein the path of travel of filter assemblies includes a curved portion, and the first inspection and the second and third inspections are sequentially conducted next to the curved portion of the high speed path of travel.

* * * * *

UNITED STATES PATENT AND TRADEMARK OFFICE
CERTIFICATE OF CORRECTION

PATENT NO. : 6,952,257 B2
DATED : October 4, 2005
INVENTOR(S) : Darek B. Hathaway It is certified that error appears in the above-identified patent and that said Letters Patent is hereby corrected as shown below:

Column 5,
Line 25, insert -- (d) -- before "conducting".

Signed and Sealed this

Thirteenth Day of December, 2005

JON W. DUDAS
*Director of the United States Patent and Trademark Office*